United States Patent [19]

Korbonits et al.

[11] 4,391,821
[45] Jul. 5, 1983

[54] 7-SUBSTITUTED BENZOPYRANES AND PROCESS FOR THE PREPARATION THEREOF

[75] Inventors: Dezső Korbonits; Mihàly Nògràdi; Borbala Vermes nee Szluha; János Strelisky; Andras Wolfner; Gergely Heja; Gàbor Kovàcz, all of Budapest; Jozsef Szegi, Debaeccen; Sandor Virag, Budapest, all of Hungary

[73] Assignee: Chinoin Gyogyszer es Vegyeszeti Termekek Gyara R.T., Budapest, Hungary

[21] Appl. No.: 284,573

[22] Filed: Jul. 17, 1981

[30] Foreign Application Priority Data

Dec. 16, 1980 [HU] Hungary ................................. 3001

[51] Int. Cl.³ .................... A61K 31/35; C07D 311/22; C07D 311/58
[52] U.S. Cl. ................................... 424/283; 549/401; 549/406; 549/408
[58] Field of Search .................... 260/345.2; 424/283; 549/401, 406, 408

[56] References Cited

U.S. PATENT DOCUMENTS 3,046,275 7/1962 Kohlstaedt et al. .......... 260/345.2 X
3,810,896 5/1974 Witte et al. .................. 260/345.2 X

OTHER PUBLICATIONS

Wang et al., ACTA Pharm. Sinica, vol. XV, pp. 253–256, (1980).
Da Re et al., J. Med. Chem., 15, 868, (1972).
Da Re et al., J. Med. Chem., 15, 198, (1972).

*Primary Examiner*—Nicky Chan
*Attorney, Agent, or Firm*—Karl F. Ross; Herbert Dubno

[57] ABSTRACT

The present invention relates to novel 7-substituted benzopyranes of formula (I), wherein
$R_1$ and $R_2$ are hydrogen, alkyl of from 1 to 6 carbon atoms, hydroxyalkyl, alkenyl, cycloalkyl, phenylalkyl, dimethoxy-phenylalkyl, or $R_1$ and $R_2$ together with the joining nitrogen atom may represent a 5–7-membered heterocyclic ring,
$R_3$ is hydrogen, alkyl of from 1 to 4 carbon atoms or phenyl,
$R_4$ is hydrogen,
$R_5$ is hydrogen or phenyl, or
$R_4$ and $R_5$ together may represent a bonding electron pair between the second and the third carbon atoms of the benzopyrane ring,
$R_6$ and $R_7$ are hydrogen or they may represent an oxygen atom together,
n is 1 or 2, with the proviso, that the pyrane ring may bear only one alkyl or phenyl substituent, and preparation process thereof.

The novel compounds have valuable therapeutical effects, mainly in cardiotherapy.

29 Claims, No Drawings

7-SUBSTITUTED BENZOPYRANES AND PROCESS FOR THE PREPARATION THEREOF

Present invention relates to new, 7-substituted benzopyrane derivatives of formula (I)

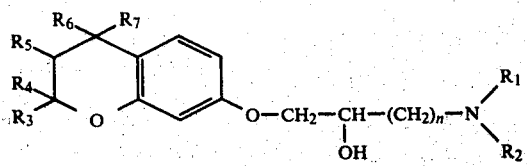

and to a process for the preparation thereof. The new compounds are useful in treatment of heart diseases.

The substituents in formula (I) can have the following meanings:

$R_1$ and $R_2$ are hydrogen, alkyl of from one to six carbon atoms, hydroxyalkyl, alkenyl, cycloalkyl, phenylalkyl or dialkoxyphenylalkyl, or $R_1$ and $R_2$ together with the nitrogen atom may form a heterocyclic ring, $R_3$ is hydrogen, alkyl of from one to four carbon atoms or phenyl, $R_4$ is hydrogen, $R_5$ is hydrogen or phenyl, or $R_4$ and $R_5$ together represent a bonding electron pair between the second and the third carbon atoms of the benzopyrane ring, $R_6$ and $R_7$ are hydrogen or they may form an oxygen atom together, N is 1 or 2, provides that the pyrane ring may bear only one alkyl or phenyl substituent.

The salts of compounds of formula (I) particularly the acid addition salts which are pharmaceutically acceptable, non-toxic salts formed with inorganic acids, for example with hydrogen chloride, hydrogen bromide, sulfuric acid or phosphoric acid, or with suitable organic acids, particularly with carboxylic acids and sulfonic acids, for example with acetic acid, succinic acid, glycolic acid, lactic acid, tartric acid, citric acid, ascorbic acid, maleic acid, benzoic acid, toluenesulfonic acid, or quaternary ammonium salts formed with compounds of formula $R_8X$, wherein $R_8$ is alkyl of from one to four carbon atoms, most preferably methyl, and X is preferably halogen, sulfate or phosphate, are also included.

Compounds of formula (I) can be used for therapeutic purposes in optically active and also in racemic form; both forms fall within the scope of our invention.

Aryloxypropanolamines of different types are known to be useful for the treatment of heart diseases, mainly for curing heart arrhythmia, angina pectoris and hypertension. The therapeutic effect of the compounds is mostly supposed to derive from their β-adrenergic receptor blocking effect.

Oxypropanolamine moieties of these therapeutically active compounds are almost always identical, the amino group is generally substituted with a branched alkyl group, usually with an isopropyl or a tert-butyl group, and the advantageous therapeutic effects are achieved by variations in the aryl rings. The α-naphthyl group and phenyl groups substituted with different substituents have been found to be advantageously applicable aryl groups. Furthermore it is known that several oxypropanolamine derivatives containing another substituent particularly a condensed heterocyclic ring- in place of the phenyl or naphthyl group, also have favorable effects in cardiotherapy. Though this latter group embraces also some oxypropanolamines substituted with an oxygen-containing heterocycle, no 7-substituted benzopyrane of formula (I) is known having advantageous cardiotherapeutical effects, moreover, benzopyranes of formula (II)

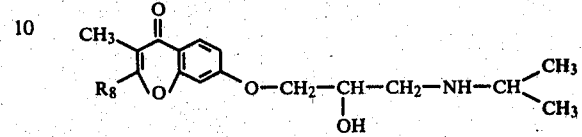

wherein $R_8$ represents methyl or phenyl, were firmly declared not to possess any cardiotherapeutical effect, though this could have been expected because of their very similar structure to that of compounds of formula (I) [J. Med. Chem., 15, 868, (1972)].

On this basis the conclusion can be drawn that from point of view of efficiency beyond the aminoalcohol moiety the structure of the heterocycle also plays a decisive role.

It has surprisingly been found that 7-substituted benzopyranes of formula (I) and pharmaceutically acceptable addition salts thereof have various very valuable therapeutical properties, mainly in cardiotherapy, depending upon the substituents of the pyrane ring and the number of carbon atoms of the alkanolamine moiety; consequently these compounds can be used in human therapy, in particular for treatment or prophylaxis of coronary diseases, for treatment of heart arrhythmia, for restraint of tone of smooth muscles and for lowering blood pressure.

Compounds of formula (Ia)

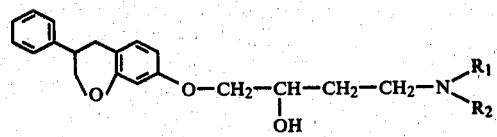

constitute a special group of compounds of formula (I) and possess very valuable pharmacological properties, namely antiarrhythmic, and antianginic effects according to the experiments carried out. In formula (Ia) $R_1$ and $R_2$ are as defined above, preferably $R_1$ is branched alkyl or cycloalkyl, and $R_2$ is hydrogen. For example the 4-cyclohexylamino-1-(2-phenyl-3,4-dihydro-2H-1-benzopyrane-7-yloxy)-2-butanol given to rats in the i.v. measured $LD_{50/10}$ dose revokes arrhythmia induced by 30 μg/kg i.v. aconitin. It suspends ventricular tadhycardia provoked by Strophantin in anesthetized cats for a long time (19 minutes), remarkably increases the ventricular fibrillation threshold in open-chested anesthetized cats and has a stronger effect that that of Propranolol.

Accordng to electrophysiological studies the effect of the above compound in $5 \times 10^{-5}$ M concentration to the effective refractory period in guinea pig isolated left auricle is stronger by nearly an order of magnitude than that of Practolol, and is almost as strong as the effect of Propranolol. The antiisoproterenol effect of the compound is moderated. There is an antiisoproterenol effect in guinea pig isolated left auricle in a concentration of $5 \times 10^{-5}$ M, while a similar effect in trachea preparation can be achieved only in a concentration of $10^{-4}$ M. Runs of the concentration curves show that the antiisoproterenol effect is not of a competitive character, so compounds of formula (Ia) of our invention despite their strong antiarrhythmic effect cannot be considered as β-receptor blocking agents.

From the pharmaceutical point of view the strong antianginic effect of our compounds of formula (Ia) is very important. The 4-cyclohexylamino-1-(3-phenyl-3,4-dihydro-2H-1-benzopyrane-7-yloxy)-2-butanol in a dose of $LD_{50/40}$ eliminates practically completely the increase of the T-wave in the electrocardiogram of rabbits anesthetized with urethane, said increase being induced by 0.5 E/kg ornithine-vasopressin. This effect significantly surpasses the effect of Propranolol.

It is favorable, that beside their important antiarrhythmic and antianginic effects compounds of formula (Ia) decrease only slightly blood pressure and heart frequency of anesthetizied cats; hence they have no heart-weakening effect.

Propanolamines of formula (Ib)

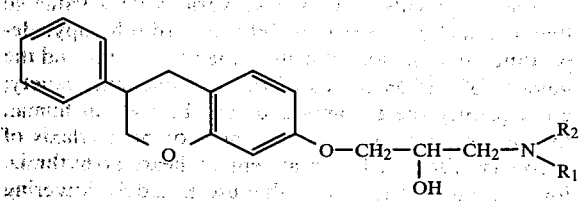

constitute another special subgroup of compounds of formula (I). In formula (Ib) $R_1$ and $R_2$ are as defined above. These compounds have also very advantageous pharmaceutical effects, which, however, differ from the effects of the butanolamines of formula (Ia). The 3-isopropylamino-1-(3-phenyl-3,4-dihydro-2H-1-benzopyrane-7-yloxy)-2-propanol introduced i.v., or administered to rabbits enterally causes significant and long-lasting blood pressure lowering without affecting the heart frequency, the volume of breathing and the frequency of breathing. A 10 μg/0,1 ml dose increases the coronary flow in rat Langendorff-heart.

Compounds of formula (Ic)

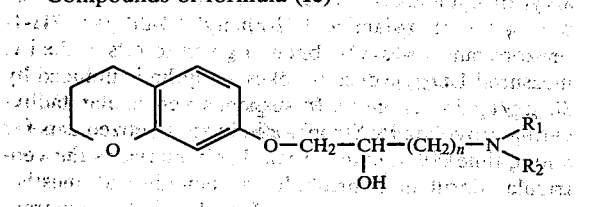

wherein $R_1$, $R_2$ and n are as defined above, also constitute a special subgroup of compounds of formula (I) and possess further advantageous therapeutical effects; their blood pressure lowering effect is extraordinarily strong. So the 3-isopropylamino-1-(3,4-dihydro-2H-1-benzopyrane-7-yloxy)-2-propanol also in a $LD_{50/320}$ mg/kg i.v. dose causes a blood pressure lowering of 33,5% in anesthetized cats ($LD_{50}$=66 mg/kg i.v. in mice).

Compounds of formula (Id)

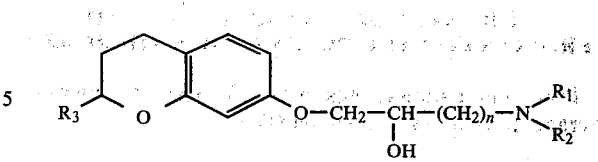

wherein $R_3$ is as defined above, but different from hydrogen, $R_1$, $R_2$ and n are as defined above, constitute a special subgroup of compounds of formula (I) and possess advantageous therapeutical properties; they show significant antiisoproterenol properties, so they can be used in therapy as β-adrenerg receptor blocking agents. Among the compounds of formula (Id) the 1-(2-methyl-3,4-dihydro-2H-1-benzopyrane-7-yloxy)-3-cyclohexylamino-2-propanol is especially advantageous, because in an $LD_{50/10}$ i.v. dose it inhibits strongly the blood pressure lowering and heart frequency increasing effects induced in cats by 2 mg/kg i.v. administered isoproterenol.

Compounds of formula (Ie)

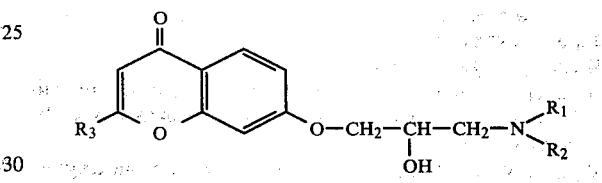

wherein $R_1$ and $R_2$ are as defined above, $R_3$ is as defined above but is different from phenyl group, constitute a special subgroup of compounds of formula (I) and possess further advantageous therapeutical effects.

These compounds in an $LD_{50/10}$ i.v. dose significantly moderate the arrhythmia induced in rats by administering 30 μg/kg i.v. aconitin, furthermore they reduce the blood pressure lowering and the increase of heart frequency provoked by isoproterenol. 1-(2-methyl-4H-1-benzopyrane-4-one-7-yloxy)-3-(1,1-dimethylethylamino)-2-propanol has especially advantageous therapeutical effects; in an $LD_{50/20}$ i.v. dose it reduces strongly (by 50.2%) the blood pressure of anesthetized cats, without significantly affecting their heart frequency. Besides, this compound is a spasmolytic agent with parasympatholytic and direct striped muscle effects on rabbit ilium, and is also effective against spasms induced in rat intestine by acetylcholine or by barium chloride.

Novel compounds of formula (I) can be prepared by per se known methods described hereinbelow:

(a) a compound of formula (III)

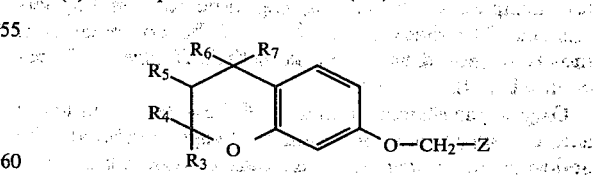

wherein $R_3$, $R_4$, $R_5$, $R_6$ and $R_7$ are as defined above and Z is a group of formula

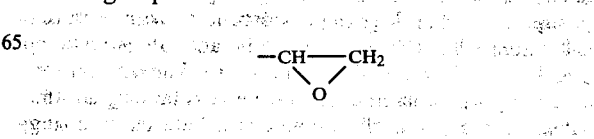

or —CHOH(CH$_2$)$_n$—Hlg, wherein n is as defined above, Hlg means halogen, preferably chloro or bromo, is reacted with an amine of formula R$_1$R$_2$NH, wherein R$_1$ and R$_2$ are as defined above, or (b) for preparing compounds of formula (I) wherein R$_1$ and R$_2$ are hydrogen, the above process can also be carried out with dicarboxylic acid imides, most preferably with succinic imide or with phthalic imide in place of ammonia, whereby the formed N-substituted imides are decomposed in a known way by hydrolysis, in the case of phthalic imide most preferably with hydrazine.

Reactions (a) and (b) are performed preferably in an organic solvent, or in a water-containing organic solvent, or in a mixture of organic solvents, preferably in alcohols, most preferably in ethanol.

The reaction temperature is maintained between 10° C. and 100° C., preferably between 50° C. and 90° C. Reaction time varies between 0.2 hours and 20 hours depending upon the reaction temperature; in general, 2-4 hours at 60°-85° C. is the most suitable.

(c) a compound of formula (IV)

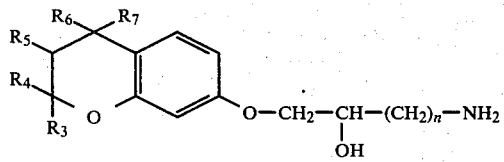

constituting a special subgroup of compounds of formula (I), wherein R$_3$, R$_4$, R$_5$, R$_7$ and n are as defined above, is reacted with a carbonyl compound of formula (V)

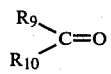

wherein R$_9$ is hydrogen or alkyl of from one to six carbon atoms, R$_{10}$ is alkyl of from one to six carbon atoms, phenylalkyl, dimethoxyphenyl or phenyl, or R$_9$ and R$_{10}$ together with the carbonyl carbon atom may also form a 5-7-membered ring, said reaction taking place by simultaneous forming of water, then the formed Schiff-base of formula (VI)

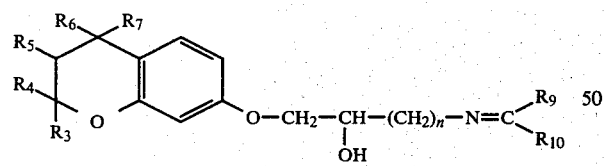

wherein the R substituents and n have the same meanings as above, is reduced. The condensation reaction is accomplished either without solvent, triturating the reagents in a melt, or using an organic solvent or a diluent, preferably applying heating when compounds of formula (VI) form.

Reduction of compounds of formula (VI) can be performed by catalytic hydrogenation, preferably with a platinum, palladium or Raney-nickel catalyst, in a solvent, preferably in ethanol. Reduction of compounds of formula (VI) can preferably be carried out using a chemical reducing agent, most preferably using sodium tetrahydroborate.

The sodium tetrahydroborate reduction can preferably be accomplished in alcohols, most preferably in methanol in the presence of only a little water, at a temperature of 0°-40° C. A very advantageous embodiment of process (c) is carries out the condensation and the reduction in one step, without isolating the intermediate Schiff-bases of formula VI. In this case primary amines of the formula (IV) and carbonyl compounds of formula (V) are reacted in a solvent and/or diluent—preferably in ethanol—with or without heating, then the mixture is subjected to reduction. Most preferably the reductive condensation is carried out by catalytic hydrogenation in ethanol in the presence of a palladium/carbon catalyst.

According to another possible embodiment amines of formula (IV) and carbonyl compounds of formula (V) are shaken or stirred in a hydrogen atmosphere together with the catalyst and the solvent, hence the reductive condensation is performed in one technological step.

(d) a compound of formula (VII)

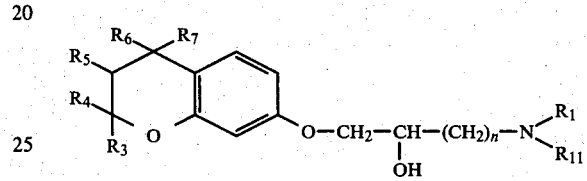

wherein R$_1$, R$_3$, R$_4$, R$_5$, R$_6$, R$_7$ and n are as defined above, R$_{11}$ is a hydrogenolyzable group, preferably a benzyl group, is subjected to hydrogenolysis. Compounds of formula (VII) constitute a special subgroup of compounds of formula (I). The hydrogenolysis can preferably be accomplished by catalytic hydrogenation, for example with platinum or palladium/carbon catalyst, or in a diluent, most preferably in ethanol. Following the above process a special subgroup of compounds of formula (I) can be obtained, wherein R$_2$ means hydrogen.

(e) a phenol derivative of formula (VIII)

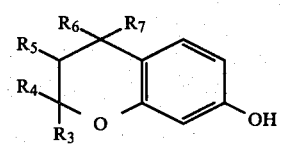

wherein R$_3$, R$_4$, R$_5$, R$_6$ and R$_7$ are as defined above, is reacted either with an amine of formula (IX)

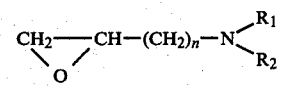

wherein R$_1$, R$_2$ and n are as defined above, or with an amine of the formula (X)

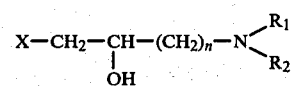

wherein X is halogen, preferably chloro or bromo, R$_1$, R$_2$ and n are as defined above. The reaction is preferably carried out in an organic solvent or diluent. In the case where phenol derivatives of formula (VIII) are reacted with halogen derivatives of formula (X), the reaction is preferably carried out in the presence of an acid acceptor. As an acid acceptor, preferably an inorganic or an organic base can be used, most preferably an alkali hydroxide, an alkali alkoxide or an alkali carbonate. Most preferably at first the alkali salts of phenols of formula (VIII) can be formed and these salts can be used as starting materials, in which case no acid acceptor is necessary. In case the halogen compounds of formula (X) are used as starting materials, reaction takes place via epoxides of formula (IX).

(f) a compound of formula (III), wherein $R_3$, $R_4$, $R_5$, $R_6$ and $R_7$ are as defined above, Z is a group of formula —CHOH—$CH_2$—Cl, is reacted with metal cyanides, preferably with potassium cyanide or sodium cyanide in a solvent medium, preferably in a water-alcohol solvent medium, then the so formed nitrile of formula (XI)

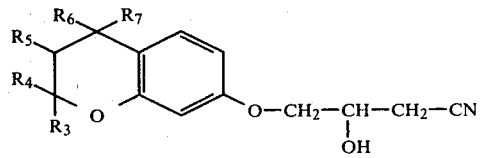

wherein the R substituents have the meanings defined above, is subjected to reduction; compounds of formula (IV), constituting a special subgroup of compounds of formula (I) wherein n is 2 and the R substituents are as defined above, are obtained. As reducing agents chemical reducing agents, preferably lithium tetrahydroaluminate in etheral solution, or catalytically activated hydrogen can be used. This latter is preferably applied in an ethanol- or methanol-containing medium saturated with ammonia, in the presence of a Raney-Ni catalyst and maintaining $10-15 \times 10^3$ Pa hydrogen overpressure. A group of compounds of formula (III), which compounds serve as starting materials for the preparation of compounds of formula (I), can be prepared as follows. Phenols of formula (VIII) are reacted with 1-chloro-2,3-epoxypropane under heating, preferably in the presence of a little pyridine; 3-chloro-3-hydroxypropyl derivatives of formula (III) are obtained (in formula (III) Z is a —CHOH—$CH_2$Cl group). In case these products are treated with a reagent capable of driving off hydrochloric acid, preferably with an inorganic basic reagent, most preferably with sodium carbonate, or with the excess of 1-chloro-2,3-epoxypropane, the corresponding 2,3-epoxypropyl derivatives are obtained (Z in formula (III) is

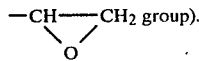

Another group of the compounds of formula (III) can be prepared by reacting compounds of formula (VIII) with 1,4-dichloro-2-butanol, preferably in a strongly alkaline medium, at a temperature of 60°–65° C. in the presence of catalytic amount of a quaternary ammonium salt. As alkaline medium most preferably an aqueous potassium hydroxide solution can be used, as a quaternary salt most preferably tetrabutyl ammoniumbisulfate can be applied. Presence of an inert atmosphere favors the reaction; the corresponding 4-chloro-2-hydroxybutyl derivatives (Z in formula (III) is —CH—OH—$CH_2$—$CH_2$—Cl group) form with a good yield. This latter group of compounds of formula (III) can be prepared also by reacting phenols of formula (VIII) with 1-chloro-3,4-epoxybutane under heating, preferably in the presence of a little pyridine; 4-chloro-2-hydroxybutyl derivatives of formula (III) are obtained (Z in formula (III) is —CHOH—$CH_2$—$CH_2$Cl group).

The novel compounds of formula (I) can be used most preferably formulated into pharmaceutical preparations. These preparations contain the effective amount of the active ingredient, if desired together with inorganic or organic, solid or liquid pharmaceutically acceptable carriers. The pharmaceutical preparations can be administered in an enteral or parenteral way. Advantageous formulation forms are tablets or capsules, which contain the active ingredient and a diluent, for example lactose, dextrose, sacharose, mannitol, sorbitol, cellulose or derivatives of the listed compounds or glycine, and/or a lubricant, for example diatomaceous earth, talc, stearic acid or salts thereof or polyethyleneglycol, and/or a bonding agent, for example silicates, starch or derivatives thereof, gelatine, methyl cellulose, and/or fillers, foam-forming mixtures, coloring ingredients, flavoring ingredients. The pharmacologically active novel compounds can also be used in form of parenterally administrable preparations or infusion solutions. These pharmaceutical preparations, which may contain further pharmacologically effective components if desired, can be manufactured by methods known per se, for example by the usual mixing, granulating, tabletting, dissolving or lyophilizing techniques. The preparations contain at about 0.2–100%, particularly at about 1–50% active ingredient. Dosing depends upon various factors, for example the way of administration, age and/or the condition of the person to be treated. Daily oral dose is at about 0.1–0.2 g for a person weighing 70 kilograms.

The following examples illustrate the invention without restricting its scope.

EXAMPLES

A. Preparation examples

Example 1

(a) A mixture of 6.64 g 1-chloro-4-(3-phenyl-3,4-dihydro-2H-1-benzopyrane-7-yloxy)-2-butanol and 3.7 cm³ cyclohexylamine was kept at 95° C. for 3 hours. The mixture was dissolved in 10 cm³ of methanol, 6 cm³ of methanol saturated with hydrochloric acid was added thereto, then the solution was evaporated. The residue was dissolved in 40 cm³ of benzene, the benzene solution was extracted with water and evaporated; 6.2 g crude 4-cyclohexylamino-1-(3-phenyl-3,4-dihydro-2H-1-benzopyrane-7-yloxy)-2-butanol-hydrochloride was obtained. The weight of the product crystallized from acetone is 5.0 g; melting point is 157°–159° C. The base liberated from its hydrochloric salt melts at 114°–116° C. The base can be transformed with methyl iodide into 1-(3-phenyl-3,4-dihydro-2H-1-benzopyrane-7-yloxy)-4-(dimethyl-cyclohexylammonium)-2-butanol-iodide (m.p. is 208°).

The starting 1-chloro-2-butanol derivative was prepared the following way:

(b) A mixture of 5.7 g 7-hydroxy-3-phenyl-3,4-dihydro-2H-1-benzopyrane, 4.3 g 1,4-dichloro-2-butanol, 0.05 g tetrabutyl ammonium hydrogensulfate and 2.8 g potassium hydroxide dissolved in 8 cm³ of water was vigorously stirred in an inert atmosphere at 65° C. for 4 hours. To the reaction mixture 20 cm³ of water was added and the product was extracted three times with 20—20 cm³ benzene. The combined benzene extracts were washed with a 10% aqueous sodium hydroxide solution, dried and evaporated. Crystallizing the residue from benzene 6.0 g 1-chloro-4-(3-phenyl-3,4-dihydro-2H-1-benzopyrane-7-yloxy)-2-butanol was obtained, with a melting point of 123°–125° C.

(c) A mixture of 5.0 g 7-hydroxy-3-phenyl-3,4-dihydro-2H-1-benzopyrane, 5.0 g 1-chloro-3,4-epoxybutane (Liebigs Ann. Chem., 596, 80, (1955)), and 0.1 ml piperidine was kept at 70° C. for three hours, then the epoxide in excess was distilled off at reduced pressure. The residue was dissolved in 20 ml of chloroform and the chloroform solution was extracted twice with 10—10 ml 10% aqueous sodium hydroxide solution. After evaporation of the chloroform solution 5,1 g 1-chloro-4-(3-phenyl-3,4-dihydro-2H-1-benzopyrane-7-yloxy)-2-butanol was obtained.

Example 2

Following the process of example 1 and using 1-chloro-4-(3-phenyl-3,4-dihydro-2H-1-benzopyrane-7-yloxy)-2-butanol and 2-(3,4-dimethoxy-phenyl)-ethylamine as starting materials, 4-(2-(3,4-dimethoxy-phenyl)-ethylamino)-1-(3-phenyl-3,4-dihydro-2H-1-benzopyrane-7-yloxy)-2-butanol-hydrochloride was obtained. Melting point is 162°–164° C. (methanol).

Example 3

10 g 1-chloro-4-(3-phenyl-3,4-dihydro-2H-1-benzopyrane-7-yloxy)-2-butanol and 25.5 cm$^3$ 2-propylamine were kept in a closed tube at 80° C. for 12 hours. The mixture was dissolved in 50 cm$^3$ of methanol, then strongly alkalized with 40% sodium hydroxide solution and evaporated. To the residue water was added and it was extracted with chloroform, the chloroform was distilled off, the residue was dissolved in 30 cm$^3$ of methanol, after an hour the solution was filtered, strongly acidified with hydrochloric methanol, then evaporated to dryness. Treating the residue with acetone 8 g 4-(1-methylethyl-amino)-1-(3-phenyl-3,4-dihydro-2H-1-benzopyrane-7-yloxy)-2-butanol-hydrochloride was obtained with a melting point of 196°–198° C.

The base liberated from the salt can be transformed with methyl iodide into 1-(3-phenyl-3,4-dihydro-2H-1-benzopyrane-7-yloxy)-4-(dimethyl-(1-methylethyl)-ammonium)-2-butanol-iodide (m.p. 158°–160° C.).

Example 4

Following the process of example 3 and using 1-chloro-4-(3-phenyl-3,4-dihydro-2H-1-benzopyrane-7-yloxy)-2-butanol and 1,1-dimethyl-ethylamine as starting materials, 4-(1,1-dimethyl-ethylamino)-1-(3-phenyl-3,4-dihydro-2H-1-benzopyrane-7-yloxy)-2-butanol-hydrochloride can be prepared (m.p. 187°–189° C.).

The base liberated from the salt can be transformed with methyl iodide into 1-(3-phenyl-3,4-dihydro-2H-1-benzopyrane-7-yloxy)-4-(dimethyl-(1,1-dimethylethyl)-ammonium)-2-butanol-iodide (m.p. 199°–200° C.).

Example 5

(a) 6.2 g 1-chloro-3-(3-phenyl-3,4-dihydro-2H-1-benzopyrane-7-yloxy)-2-propanol and 8.6 cm$^3$ 2-propylamine were boiled in 60 cm$^3$ ethanol for 2 hours. The mixture was evaporated, the residue was triturated with 5% sodium hydroxide solution, the base was extracted with dichloromethane, dried, filtered and the solvent was distilled off. The remained base was dissolved in 15 cm$^3$ ethanol at 50° C. and a salt was formed with 2.5 g maleic acid. 6.5 g 1-(3-phenyl-3,4-dihydro-2H-1-benzopyrane-7-yloxy)-3-(1-methylethylamino)-2-propanol-maleate was obtained.

(b) The starting 1-chloro-2-propanol derivative was prepared as follows:

11.3 g 3-phenyl-7-hydroxy-3,4-dihydro-2H-1-benzopyrane, 0.1 cm$^3$ piperidine and 22 cm$^3$ 1-chloro-2,3-epoxypropane were stirred at 90° C. for 9 hours. The solution was evaporated under reduced pressure, then twice 60–60 cm$^3$ of benzene were distilled off from the residue, it was dissolved in 50 cm$^3$ of tetrahydrofurane and into the solution hydrochloric gas was introduced for 5 minutes. The solution was evaporated after an hour's standing, and the residue was crystallized from aceton. 10 g 1-chloro-3-(3-phenyl-3,4-dihydro-2H-1-benzopyrane-7-yloxy)-2-propanol (m.p. 74°–76° C.) was obtained.

Examples 6–8

Following the process of example 5 (a) the compounds listed hereinbelow were prepared from the enumerated starting materials:

1-(3-phenyl-3,4-dihydro-2H-1-benzopyrane-7-yloxy)-3-cyclopropylamino-2-propanol-maleate (m.p. 150°–152° C. crystallized from the 8:1 mixture of methanol and acetone) was prepared from 1-chloro-3-(3-phenyl-3,4-dihydro-2H-1-benzopyrane-7-yloxy)-2-propanol with cyclopropylamine;

1-(3-phenyl-3,4-dihydro-2H-1-benzopyrane-7-yloxy)-3-(1,1-dimethylamino)-2-propanol-maleate (m.p. 199°–201° C. (decomposes) crystallized from the 2:1 mixture of methanol and acetone) was prepared from 1-chloro-3-(3-phenyl-3,4-dihydro-2H-1-benzopyrane-7-yloxy)-2-propanol with 1,1-dimethylamine;

1-(3-phenyl-3,4-dihydro-2H-1-benzopyrane-7-yloxy)-3-cyclohexylamino-2-propanol-maleate (m.p. 177°–178° C. crystallized from the 3:1 mixture of acetone and methanol) was prepared from 1-chloro-3-(3-phenyl-3,4-dihydro-2H-1-benzopyrane-7-yloxy)-2-propanol with cyclohexylamine.

EXAMPLE 9

(a) 5.0 g 1,2-epoxy-3-(3-phenyl-3,4-dihydro-2H-1-benzopyrane-7-yloxy)-propane and 2.5 cm$^3$ 2-propylamine were boiled in 40 cm$^3$ ethanol for 2 hours. After evaporating the mixture and triturating the residue with water, the base 1-(3-phenyl-3,4-dihydro-2H-1-benzopyrane-7-yloxy)-3-(1-methylethylamino)-2-propanol was obtained, from which forming salt following the process of example 5 (a) 5.5 g of the maleate was obtained (m.p. 171°–173° C.).

(b) The starting epoxide was prepared in the following manner:

17 g 7-hydroxy-3-phenyl-3,4-dihydro-2H-1-benzopyrane, 0.1 cm$^3$ piperidine and 100 cm$^3$ 1-chloro-2,3-epoxypropane were stirred for 6 hours at a temperature of 90° C. The solution was evaporated under reduced pressure, the residue was dissolved in 150 cm$^3$ benzene and the obtained solution was extracted twice with 25—25 cm$^3$ saturated sodium carbonate solution. The benzene phase was separated from the precipitated resin, clarificated with charcoal, filtered and evaporated. Crystallizing the residue from methanol, 15 g pure crystalline 1,2-epoxy-3-(3-phenyl-3,4-dihydro-2H-1-benzopyrane-7-yloxy)-propane was obtained (m.p. 117°–119° C.).

EXAMPLE 10

(a) 4.3 g 1-chloro-3-(2-methyl-4H-1-benzopyrane-4-one-7-yloxy)-2-propanol and 2.5 cm³ 2-propylamine were boiled in 40 cm³ ethanol for 2 hours; the obtained mixture was worked up according to example 5 (a), and 4.8 g 1-(2-methyl-4H-1-benzopyrane-4-one-7-yloxy)-3-(1-methylethylamino)-2-propanol-maleate was obtained (m.p. 161°–163° C.).

(b) The starting 1-chloro-2-propanol derivative was prepared as follows:

17.6 g 7-hydroxy-2-methyl-4H-1-benzopyrane-4-one-[J.Org. Chem. 24, 683, (1959)], 0.1 cm³ piperidine and 60 cm³ 1-chloro-2,3-epoxy-propane were stirred for 9 hours at a temperature of 90° C. The mixture was worked up according to example 5 (b) and 19.0 g 1-chloro-3-(2-methyl-4H-1-benzopyrane-4-one-7-yloxy)-2-propanol was obtained (m.p. 104°–106° C.).

EXAMPLES 11–14

Following the process of example 10 (a) and using 1-chloro-3-(2-methyl-4H-1-benzopyrane-4-one-7-yloxy)-2-propanol as a starting material, the end-products listed hereinbelow were obtained by applying the enumerated reagents.

1-(2-methyl-4H-1-benzopyrane-4-one-7-yloxy)-3-(1,1-dimethylethylamino)-2-propanol was obtained as a base (m.p. 114°–116° C.) with 1,1-dimethylethylamine as a reagent; with maleic acid the maleate thereof (m.p. 185°–187° C.) can be formed;

1-(2-methyl-4H-1-benzopyrane-4-one-7-yloxy)-3-(cyclohexylamino)-2-propanol-maleate (m.p. 177°–179° C. with decomposition) was obtained with cyclohexylamine and subsequent salt forming reaction;

1-(2-methyl-4H-1-benzopyrane-4-one-7-yloxy)-3-(cyclopropylamino)-2-propanol-maleate (m.p. 151°–153° C.) was obtained with cyclopropylamine and subsequent salt forming reaction;

1-(2-methyl-4H-1-benzopyrane-4-one-7-yloxy)-3-(2-allylamino)-2-propanol-maleate (m.p. 138°–140° C. with decomposition) was obtained with allylamine and subsequent salt forming reaction.

EXAMPLE 15

(a) 3.7 g 1,2-epoxy-3-(2-methyl-4H-1-benzopyrane-4-one-7-yloxy)-propane and 2.5 cm³ 2-propylamine were boiled in 40 cm³ ethanol for 2 hours; the process of example 9 (a) was followed. 4.3 g 1-(2-methyl-4H-1-benzopyrane-4-one-7-yloxy)-3-(1-methylethyl-amino)-2-propanol (m.p. 80°–82° C.) was obtained in the form of a base.

(b) The starting epoxide was prepared as follows: 17.6 g 7-hydroxy-2-methyl-4H-1-benzopyrane-4-one- was reacted with a solution of 0.1 cm³ piperidine and 100 cm³ 1-chloro-epoxypropane according to example 9 (b). Working up the mixture 16.8 g 1,2-epoxy-3-(2-methyl-4H-1-benzopyrane-4-one-7-yloxy)-propane was obtained (m.p. 121°–123° C.).

EXAMPLE 16

(a) Reacting 4.2 g 1-chloro-3-(2-methyl-3,4-dihidro-2H-1-benzopyrane-7-yloxy)-2-propanol and 8 cm³ 2-propylamine in 40 cm³ ethanol according to the process of example 5 (a) 4.0 g 1-(2-methyl-3,4-dihydro-2H-1-benzopyrane-7-yloxy)-3-(1-methylethylamino)-2-propanol (m.p. 79°–81° C.) was obtained as a base, from which a salt can be formed with maleic acid (m.p. 118°–120° C.).

(b) Following the process of example 9 (a) and reacting 1,2-epoxy-3-(2-methyl-3,4-dihydro-2H-1-benzopyrane-7-yloxy)-propane with 2-aminopropane, 1-(2-methyl-3,4-dihydro-2H-1-benzopyrane-7-yloxy)-3-(1-methylethylamino)-2-propanol was obtained as a base (m.p. 79°–81° C.).

(c) The starting phenol, and the chloropropanol and epoxy derivatives therefrom can be prepared the following way:

9.8 g 7-hydroxy-2-methyl-4H-1-benzopyrane-4-on in 20 cm³ dry pyridine and 20 cm³ acetic anhydride was left to stand for 24 hours. The obtained solution was admixed with the mixture of ice, water and hydrochloric acid and the precipitate [11 g of 7-acetoxy-2-methyl-4H-1-benzopyrane-4-on, m.p. 94°–95° C. from benzene] was filtered. The acetoxy compound was hydrogenated in glacial acetic acid at 60° C. in the presence of a palladium on charcoal catalyst till it absorbed 3 molar equivalents of hydrogen, then after filtration and evaporation 11.5 g 7-acetoxy-2-methyl-3,4-dihydro-2H-1-benzopyrane-4-on (m.p. 66°–68° C. from ethanol) was obtained. This compound was hydrolyzed hot in the mixture of 100 cm³ methanol and 1.5 cm³ concentrated hydrochloric acid. The solvent was distilled off, the residue was subjected to fractionated distillation to obtain 6.5 g 7-hydroxy-2-methyl-3,4-dihydro-2H-1-benzopyrane (b.p. 85°–90° C./26 Pa); starting from this compound and following the process of example 5 (b), using a piperidine catalyst and 1-chloro-2,3-epoxypropane reagent, 1-chloro-3-(2-methyl-3,4-dihydro-2H-1-benzopyrane-7-yloxy)-2-propanol (m.p. 70°–72° C.) was obtained.

Starting from 7-hydroxy-2-methyl-3,4-dihydro-2H-1-benzopyrane, using 1-chloro-2,3-epoxypropane reagent and following the process of example 9 (b), 1,2-epoxy-3-(2-methyl-3,4-dihydro-2H-1-benzopyrane-7-yloxy)-propane was obtained (m.p. 67°–69° C.).

EXAMPLES 17–18

Following the process of example 16 (a) and using 1-chloro-3-(2-methyl-3,4-dihydro-2H-1-benzopyrane-7-yloxy)-2-propanol as a starting material, the compounds listed hereinbelow could be prepared applying the enumerated reagents:

1-(2-methyl-3,4-dihydro-2H-1-benzopyrane-7-yloxy)-3-(1,1-dimethylethylamino)-2-propanol base (m.p. 92°–94° C.) was obtained with 1,1-dimethylethylamine; melting point of the maleate is 149°–151° C.;

1-(2-methyl-3,4-dihydro-2H-1-benzopyrane-7-yloxy)-3-cyclohexylamino-2propanol base (m.p. 97°–99° C.) was prepared with cyclohexylamine; melting point of the maleate is 129°–131° C.

The above compounds can also be obtained following the process of example 16 (b), starting from 1,2-epoxy-3-(2-methyl-3,4-dihydro-2H-1-benzopyrane-7-yloxy)-propane, and reacting it with the proper primary amines.

EXAMPLES 19–20

Following the process of example 3 and reacting 9.0 g 1-chloro-4-(2-methyl-3,4-dihydro-2H-1-benzopyrane-7-yloxy)-2-butanol with 25.5 cm³ 2-propylamine 6.0 g 4-(1-methylethylamino)-1(2-methyl-3,4-dihydro-2H-1-benzopyrane-7-yloxy)-2-butanol hydrochloride (m.p. 131°–133° C.) was obtained; in a similar manner using 1,1-dimethylethylamine as a reagent 4-(1,1-dimethylethylamino)-1-(2-methyl-3,4-dihydro-2H-1-benzopyrane-7-yloxy)-2-butanol-hydrochloride (m.p. 97°–99° C.) was prepared.

The starting chlorobutanol derivative was prepared from 7-hydroxy-2-methyl-3,4-dihydro-2H-1-benzopyrane and 1,4-dichloro-2-butanol according to example 1 (b); the obtained 1-chloro-4-(2-methyl-3,4-dihydro-2H-1-benzopyrane-2-yloxy)-2-butanol was purified by distillation. B.p.: 150°–155° C./13 Pa; m.p.: 47°–48° C.

EXAMPLE 21

Reacting 6.64 g 1-chloro-4-(2-phenyl-3,4-dihydro-2H-1-benzopyrane-7-yloxy)-2-butanol with 3.7 cm³ cyclohexylamine according to example 1 (a) 1-(2-phenyl-3,4-dihydro-2H-1-benzopyrane-7-yloxy)-2-butanol cyclohexylamine hydrochloride (m.p. 104°–106° C. from isopropylalcohol) was manufactured.

The starting 1-chloro-4-(2-phenyl-3,4-dihydro-2H-1-benzopyrane-7-yloxy)-2-butanol was prepared from 2-phenyl-7-hydroxy-3,4-dihydro-2H-1-benzopyrane (J.Chem. Soc., 3137; 1954) and 1,4-dichlorobutanol according to example 1 (b), or from 1-phenyl-7-hydroxy-3,4-dihydro-2H-1-benzopyrane and 1-chloro-3,4-epoxybutane according to example 1 (c).

EXAMPLES 22–24

Following the process of example 5 (a) and starting from 1-chloro-3-(3,4-dihydro-2H-1-benzopyrane-7-yloxy)-2-propanol the compounds listed hereinbelow can be prepared:

1-(3,4-dihydro-2H-1-benzopyrane-7-yloxy)-3-(1-methylethylamino)-2-propanol (m.p. of the hydrochloride: 133°–135° C.) with 2-propylamine;

1-(3,4-dihydro-2H-1-benzopyrane-7-yloxy)-3-(1,1-dimethylethylamino)-2-propanol (m.p. of the hydrochloride; 280°–281° C. with decomposition) with 1,1-dimethylethylamine;

1-(3,4-dihydro-2H-1-benzopyrane-7-yloxy)-3-cyclohexylamino-2-propanol (m.p. of the hydrochloride: 182°–184° C.; m.p. of the base: 166°–168° C.) with cyclohexylamine.

The starting chloropropanol derivative was prepared according to example 5 (b) from 7-hydroxy-3,4-dihydro-2H-1-benzopyrane and 1-chloro-2,3-epoxypropane.

EXAMPLE 25

Following the process of example 3 and reacting 1-chloro-4-(3,4-dihydro-2H-1-benzopyrane-7-yloxy)-2-butanol with 1,1-dimethylethylamine, 4-(1,1-dimethylethylamino)-1-(3,4-dihydro-2H-1-benzopyrane-7-yloxy)-2-butanol was obtained (m.p. of the hydrochloride: 148°–150° C.).

The starting 1-chloro-4-(3,4-dihydro-2H-1-benzopyrane-7-yloxy)-2-butanol was prepared according to example 1 (b) from 7-hydroxy-3,4-dihydro-2H-1-benzopyrane (J. Chem. Soc. 1190, 1958) and 1,4-dichloro-2-butanol (m.p. 78°–80° C.).

EXAMPLE 26

(a) To a solution consisting of 12.15 g 1-chloro-3-(3,4-dihydro-2H-1-benzopyrane-7-yloxy)-2-propanol and 28 cm³ methanol, a solution of 3.6 g potassium cyanide with 7 cm³ water was added dropwise over 0.2 hour, under stirring and boiling. After a further one hour boiling the solution was evaporated under reduced pressure, the residue was crystallized from benzene. 9.18 g 4-(3,4-dihydro-2H-1-benzopyrane-7-yloxy)-3-hydroxy-butanoic acid nitrile was obtained, which was subjected to reduction in an etheral solution with 4.1 g lithium tetrahydroaluminate.

The amine obtained after working up the reaction mixture was isolated as a hydrochloride salt. The base liberated from the salt was boiled in 27 cm³ benzene with 4.1 g cyclohexanol under a water separator for 3 hours. After evaporating the benzene the residue was taken up in the mixture of 50 cm³ methanol and 2.5 cm³ water, and was subjected to reduction with 1.5 g sodium tetrahydroborate for 6 hours. The mixture then was treated with 50 cm³ water, extracted with twice 20—20 cm³ dichloromethane, evaporated and the residue was transformed with hydrochloric ethanol into a salt. 5.8 g 4-cyclohexylamino-1-(3,4-dihydro-2H-1-benzopyrane-7-yloxy)-2-butanol hydrochloride (m.p. 186°–187° C.) was obtained.

(b) 9.18 g 4-(3,4-dihydro-2H-1-benzopyrane-7-yloxy)-3-hydroxy-butanoic acid nitrile prepared as described in the previous part, was further worked up as follows: the nitrile was dissolved in 200 ml methanol saturated with ammonia, then was subjected to hydrogenolysis in the presence of 8 g Raney-nickel catalyst at a pressure of $10-15 \times 10^3$ Pa, at 50°–60° C. till the hydrogen uptake ceased. After filtration and evaporation under reduced pressure the residue was boiled in 30 cm³ benzene with 4.0 g cyclohexanone for 3 hours, then the benzene was distilled off and the residue was dissolved in 60 cm³ ethanol, and it was subjected to hydrogenolysis in the presence of a palladium on carbon catalyst, at atmospheric pressure and 20° C. After filtration 60 cm³ ether was added to the filtrate, and it was acidified with hydrochloric ethanol; 7.2 g 4-cyclohexylamino-1-(3,4-dihydro-2H-1-benzopyrane-7-yloxy)-2-butanol hydrochloride was obtained (m.p. 185°–187° C.).

EXAMPLE 27

4.0 g 1-chloro-3-(2,3-dihydro-4H-1-benzopyrane-4-on-7-yloxy)-2-propanol and 2.5 cm³ propanol were boiled in 40 cm³ ethanol for 2 hours. The mixture was evaporated, the residue was dissolved in benzene and the Schiff-base formed as by-product was decomposed by hydrochloric acid extraction. From the liberated base a salt was formed with maleic acid in an acetone solution; 1-(2,3-dihydro-4H-1-benzopyrane-4-on-7-yloxy)-3-(1-methylethylamino)-2-propanol maleate (m.p. 127°–128° C.) was obtained.

The starting chloropropanol derivative was prepared according to example 5 (b) from 7-hydroxy-2,3-dihydro-4H-1-benzopyrane-4-on (J.Chem. Soc. 1190, 1958) with 1-chloro-2,3-epoxypropane in the presence of a piperidine catalyst.

EXAMPLES 28–29

Following the process of example 26 and starting from 1-chloro-3-(2,3-dihydro-4H-1-benzopyrane-4-one-7-yloxy)-2-propanol, 1-(2,3-dihydro-4H-1-benzopyrane-4-one-7-yloxy)-3(1,1-dimethylethylamino)-2-propanol (m.p. of the hydrochloride: 178°–179° C.) was obtained using 1,1-dimethylamine as a reagent, while with cyclohexylamine 1-(2,3-dihydro-4H-1-benzopyrane-4-one-7-yloxy)-3-cyclohexylamino-2-propanol (m.p. of the hydrochloride: 188°–190° C.) was prepared.

EXAMPLE 30

25.0 g dry 7-hydroxy-3-phenyl-3,4-dihydro-2H-1-benzopyrane sodium salt was suspended in 300 ml isopropylalcohol. To the stirred and refluxed mixture 25 g freshly prepared 1-[N-benzyl-N-(1-methylethyl)-amino]-3-chloro-2-propanol was added dropwise during an hour, then the mixture was refluxed for a further period of 3 hours. The sodium chloride precipitate was filtered off, the filtrate was evaporated, the obtained residue was dissolved in 300 cm³ ether, then hydrochloride gas was introduced into the etheral suspension till formation of the precipitate ended. The saturated suspension was evaporated to dryness. The obtained 1-(3-phenyl-3,4-dihydro-2H-1-benzopyrane-7-yloxy)-3-[N-benzyl-N-(1-methylethyl)-amino]-2-propanol hydrochloride was dissolved in 1000 cm³ ethanol and was subjected to hydrogenolysis in the presence of 250 g 8% palladium on charcoal catalyst at atmospheric pressure and 20°–25° C. for 8 hours. The mixture was filtered hot, evaporated, the residue was triturated with aqueous sodium hydroxide, extracted four times with 50–50 cm³ dichloromethane, dried, filtered and evaporated. The so obtained residue was taken up in 200 cm³ ethanol, and a salt thereof was formed with 10.0 g maleic acid. 27 g 1-(3-phenyl-3,4-dihydro-2H-1-benzopyrane-7-yloxy)-3-(1-methylethylamino)-2-propanol maleate (m.p. 170°–172° C.) was obtained.

EXAMPLE 31

A mixture of 8.8 g 7-hydroxy-2-methyl-4H-1-benzopyrane-4-one, 10 g 1-chloro-3-(1,1-dimethylethylamino)-2-propanol hydrochloride, 60 g sodium hydroxide, 10 cm³ water and 20 cm³ ethanol was kept at 95°–100° C. in a closed vessel for 12 hours. The mixture was drained off and the filtrate was evaporated under reduced pressure. The residue was stirred with the mixture of 500 cm³ dichloromethane and 550 cm³ 5% aqueous hydrochloric acid for an hour, the aqueous phase was separated, alkalized with a 40% sodium hydroxide solution under cooling, extracted three times with 50—50 cm³ dichloromethane, dried, filtered and evaporated; the residue was taken up in 50 cm³ ethanol and a salt thereof was formed with 5.0 g maleic acid. 11.0 g 1-(2-methyl-4H-1-benzopyrane-4-one-7-yloxy)-3-(1,1-dimethylethylamino)-2-propanol maleate (m.p. 184°–187° C.) was obtained.

Example 32

A mixture of 28.2 g 1,2-epoxy-3-(3-phenyl-3,4-dihydro-2H-1-benzopyrane-7-yloxy)-propane, 9.9 g succinimide, 0.5 g pyridine and 100 cm³ ethanol was refluxed for 5 hours. After cooling the mixture was filtered, the solvent was distilled off and the obtained 1-(3-phenyl-3,4-dihydro-2H-1-benzopyrane-7-yloxy)-3-succinimido-2-propanol was heated with 80 cm³ 30% hydrochloric acid on a steam bath for 10 hours. The mixture was evaporated, the residue was taken up with 4000 cm³ water, the solution was extracted three times with 200—200 cm³ ether, and the aqueous phase was evaporated under reduced pressure. 2.20 g 1-(3-phenyl-3,4-dihydro-2H-1-benzopyrane-7-yloxy)-3-amino-2-propanol hydrochloride was obtained.

Example 33

5.0 g 1-(3-phenyl-3,4-dihydro-2H-1-benzopyrane-7-yloxy)-3-amino-2-propanol hydrochloride was dissolved in 200 cm³ methanol, to the solution 50 cm³ acetone was added and its pH was adjusted to 7 with 10% sodium hydroxide. The mixture was boiled for 15 minutes, then cooled, and 3.0 g sodium tetrahydroborate was added thereto during 10 minutes under stirring. The mixture was left to stand for 1 day at 20° C., then acidified with icy hydrochloric acid, evaporated to dryness under reduced pressure, to the residue 100 cm³ water was added, then alkalized with 10% sodium hydroxide solution, extracted twice with 50—50 cm³ ether, and after drying evaporated. Forming a salt of the residue 3.7 g 1-(3-phenyl-3,4-dihydro-2H-1-benzopyrane-7-yloxy)-3-(1-methylethylamino)-2-propanol maleate (m.p. 170°–172° C.) was obtained.

Example 34

(a) A solution of 10.0 g 7-(2-hydroxy-3-chloro-1-propyloxy)-4H-1-benzopyrane-4-one with 100 cm³ ethanol was boiled with 20 cm³ 1,1-dimethylethylamine for 2.5 hours. The solution was evaporated under reduced pressure, the residue was dissolved in 200 ml ethanol, to the obtained solution 40 ml 10% aqueous hydrochloric acid was added and the mixture was boiled for 10 minutes. The solvent was removed under reduced pressure and the residue was crystallized from aceton; 1-(4H-1-benzopyrane-4-one-7-yloxy)-3-(1,1-dimethylethylamino)-2-propanol hydrochloride salt (m.p. 176°–178° C.) was obtained.

(b) The starting 1-chloro-2-propanol derivative was prepared from 7-hydroxy-4H-1-benzopyrane-4-one (J. Chem. Soc., 1190, 1958) and 1-chloro-2,3-epoxypropane according to example 5. (b).

Examples 35–36

(a) A mixture of 3.70 g 1-chloro-4-(3-phenyl-3,4-dihydro-2H-1-benzopyrane-7-yloxy)-2-butanol and 6.0 ml 2-aminoethanol was kept at a temperature of 95° C. for 5 hours. To the melt saturated aqueous sodium carbonate solution was added, the precipitated product was filtered, recrystallized from ethanol and a tartrate thereof was formed with tartric acid. 1-(3-phenyl-3,4-dihydro-2H-1-benzopyrane-7-yloxy)-4-(2-hydroxyethylamino)-2-butanol tartrate (m.p. 110° C.) was obtained.

(b) According to the process of example 35. (a), reacting 3.70 g 1-chloro-4-(3-phenyl-3,4-dihydro-2H-1-benzopyrane-7-yloxy)-2-butanol with 8.0 ml 3-amino-1-propanol, and forming hydrochloride from the obtained base 1-(3-phenyl-3,4-dihydro-2H-1-benzopyrane-7-yloxy)-4-(3-hydroxy-1-propylamino)-2-butanol hydrochloride (m.p. 142°–144° C.) was obtained.

B. Pharmaceutical preparations (a) Tablets

| | |
|---|---|
| Racemic 4-cyclohexylamino-1-(3-phenyl-3,4-dihydro-2H—1-benzopyrane-7-yloxy)-2-butanol hydrochloride | 40.0 g |
| Maize starch | 164.0 g |
| Calcium phosphate | 240.0 g |
| Magnesium stearate | 1.0 g |
| | 445.0 g |

The admixed components were granulated in a known way; 1000 tablets were obtained, each weighing 445 mg and containing 40 mg active ingredient.

(b) Capsules

| | |
|---|---|
| Racemic 3-isopropylamino-(3,4-dihydro-2H—1-benzopyrane-7-yloxy)-2-propanol hydrochloride | 15 g |
| Maize starch | 185 g |
| | 200 g |

The thoroughly admixed components were filled in 20 mg doses into gelatine capsules of proper size. Each capsule contains 15 mg active ingredient.

(c) Dragée with protracted action

| | |
|---|---|
| Racemic 1-(2-methyl-4H—1-benzopyrane-4-ene 7-yloxy)-3-(1,1-dimethylamino)-2-propanol maleate | 25.0 g |
| Carboxymethyl cellulose | 295.0 g |
| Stearic acid | 20.0 g |
| Cellulose acetatephthalate | 40.0 g |
| | 380.0 g |

The active ingredient, the carboxymethyl cellulose and the stearic acid were admixed, the mixture was granulated with a solution of the cellulose acetatephthalate with 200 ml ethylacetate/ethanol into 380 mg nuclei, which were coated with a sugar-containing 5% aqueous polyvinyl pyrrolidon solution in a known way. Each dragée contains 25 mg active ingredient.

We claim:

1. A compound of the formula (I)

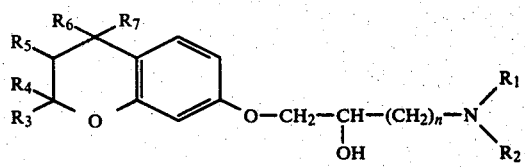

or a pharmaceutically acceptable acid addition or quaternary $C_1$–$C_4$-alkyl ammonium halide, sulfate or phosphate salt thereof, wherein $R_1$ and $R_2$ are each hydrogen, $C_1$ to $C_6$ alkyl, hydroxy-alkyl, alkenyl, cycloalkyl, phenyl-alkyl or dimethoxy-phenyl-alkyl;

$R_3$ is hydrogen, $C_1$ to $C_4$ alkyl or phenyl;

$R_4$ is hydrogen;

$R_5$ is hydrogen or phenyl; but if $R_3$ is other than phenyl, $R_4$ and $R_5$ together represent a bonding electron pair between the 2- and 3-positions of the benzopyrane nucleus;

$R_6$ and $R_7$ are each hydrogen or together form an oxo group; and n is 1 to 2, with the proviso that the pyrane ring may bear only one alkyl or phenyl substituent.

2. A compound of the formula (Ia)

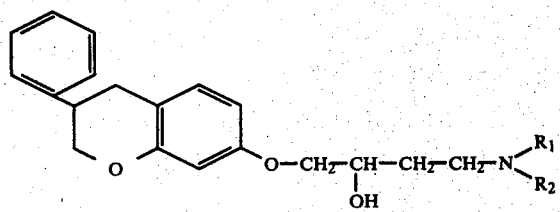

or a pharmaceutically acceptable acid addition or quaternary $C_1$–$C_4$-alkyl ammonium halide, sulfate or phosphate salt thereof, wherein $R_1$ and $R_2$ are each hydrogen, $C_1$ to $C_6$ alkyl, hydroxy-alkyl, alkenyl, cycloalkyl, phenylalkyl, or dimethoxyphenyl-alkyl.

3. The compound of the formula (Ia) defined in claim 2 or a pharmaceutically acceptable acid addition or quaternary $C_1$–$C_4$-alkyl ammonium halide, sulfate or phosphate salt thereof selected from the group consisting of (a) 4-cyclohexylamino-1-(3-phenyl-3,4-dihydro-2H-1-benzopyrane-7-yloxy)-2-butanol;

(b) 4-(2-(3,4-dimethoxy-phenyl)-ethylamino)-1-(3-phenyl-3,4-dihydro-2H-1-benzopyrane-7-yloxy)-2-butanol;

(c) 4-(1,1-dimethyl-ethylamino)-1-(3-phenyl-3,4-dihydro-2H-1-benzopyrane-7-yloxy)-2-butanol;

(d) 4-(1-methylethyl-amino)-1-(3-phenyl-3,4-dihydro-2H-1-benzopyrane-7-yloxy)-2-butanol;

(e) 1-(3-phenyl-3,4-dihydro-2H-1-benzopyrane-7-yloxy)-4-(2-hydroxyethyl-amino)-2-butanol; and (f) 1-(3-phenyl-3,4-dihydro-2H-1-benzopyrane-7-yloxy)-4-(3-hydroxy-1-propylamino)-2-butanol.

4. An antiarrhythmic and antianginal composition which comprises a pharmaceutically effective amount of the compound of the formula (Ia) defined in claim 2 or a pharmaceutically acceptable acid addition or quaternary $C_1$–$C_4$-alkyl ammonium halide, sulfate or phosphate salt thereof and a pharmaceutically acceptable carrier.

5. An antiarrhythmic and antianginal method of treatment which comprises the step of administering to a susceptible animal subject a pharmaceutically effective amount of the compound of the formula (Ia) defined in claim 2 or a pharmaceutically acceptable acid addition or quaternary $C_1$–$C_4$-alkyl ammonium halide, sulfate or phosphate salt thereof.

6. A compound of the formula (Ib)

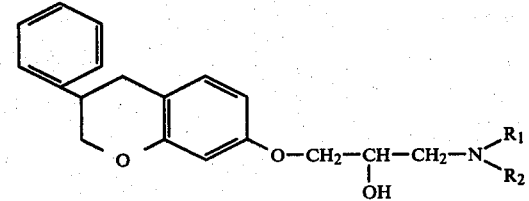

or a pharmaceutically acceptable acid addition or quaternary $C_1$–$C_4$-alkyl ammonium halide, sulfate or phosphate salt thereof, wherein $R_1$ and $R_2$ are each hydrogen, $C_1$ to $C_6$ alkyl, hydroxy-alkyl, alkenyl, cycloalkyl, phenyl-alkyl, or dimethoxy-phenyl-alkyl.

7. The compound of the formula (Ib) defined in claim 6 or a pharmaceutically acceptable acid addition or quaternary $C_1$–$C_4$-alkyl ammonium halide, sulfate or phosphate salt thereof selected from the group consisting of (a) 1-(3-phenyl-3,4-dihydro-2H-1-benzopyrane-7-yloxy)-3-(1-methyl-ethylamino)-2-propanol;

(b) 1-(3-phenyl-3,4-dihydro-2H-1-benzopyrane-7-yloxy)-3-(1,1-dimethyl-ethylamino)-2-propanol;

(c) 1-(3-phenyl-3,4-dihydro-2H-1-benzopyrane-7-yloxy)-3-cyclopropylamino-2-propanol;

(d) 1-(3-phenyl)-3,4-dihydro-2H-1-benzopyrane-7-yloxy)-3-cyclohexylamino-2-propanol; and (e) 1-(3-phenyl-3,4-dihydro-2H-1-benzopyrane-7-yloxy)-3-amino-2-propanol.

8. 1-(3-phenyl-3,4-dihydro-2H-1-benzopyrane-7-yloxy)-3-(1-methyl-ethylamino)-2-propanol or a pharmaceutically acceptable acid addition or quaternary $C_1$–$C_4$-alkyl ammonium halide, sulfate or phosphate salt thereof as defined in claim 6.

9. A hypotensive composition which comprises a pharmaceutically effective amount of the compound of the formula (Ib) defined in claim 6 or a pharmaceutically acceptable acid addition or quaternary $C_1$–$C_4$-alkyl ammonium halide, sulfate or phosphate salt thereof and a pharmaceutically acceptable carrier.

10. A hypotensive method of treatment which comprises the step of administering to a susceptible animal subject a pharmaceutically effective amount of the compound of the formula (Ib) defined in claim 6 or a pharmaceutically acceptable acid addition or quaternary $C_1$–$C_4$-alkyl ammonium halide, sulfate or phosphate salt thereof.

11. A compound of the formula (Ic)

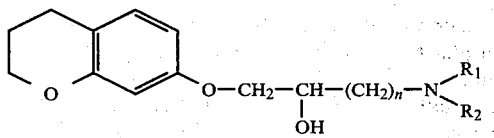

or a pharmaceutically acceptable acid addition or quaternary $C_1$–$C_4$-alkyl ammonium halide, sulfate or phosphate salt thereof, wherein $R_1$ and $R_2$ are each hydrogen, $C_1$ to $C_6$ alkyl, hydroxy-alkyl, alkenyl, cycloalkyl, phenyl-alkyl, or dimethoxy-phenylalkyl; and n is 1 or 2.

12. The compound of the formula (Ic) defined in claim 11 or a pharmaceutically acceptable acid addition or quaternary $C_1$–$C_4$-alkyl ammonium halide, sulfate or phosphate salt thereof selected from the group consisting of (a) 1-(3,4-dihydro-2H-1-benzopyrane-7-yloxy)-3-(1-methyl-ethylamino)-2-propanol;

(b) 1-(3,4-dihydro-2H-1-benzopyrane-7-yloxy)-3-(1,1-dimethyl-ethylamino)-2-propanol;

(c) 1-(3,4-dihydro-2H-1-benzopyrane-7-yloxy)-3-cyclohexyl-amino-2-propanol;

(d) 4-(1,1-dimethylethylamino)-1-(3,4-dihydro-2H-1-benzopyrane-7-yloxy)-2-butanol; and (e) 4-cyclohexylamino-1-(3,4-dihydro-2H-1-benzopyrane-7-yloxy)-2-butanol.

13. 1-(3,4-dihydro-2H-1-benzopyrane-7-yloxy)-3-(1-methyl-ethylamino)-2-propanol or a pharmaceutically acceptable acid addition or quaternary $C_1$–$C_4$-alkyl ammonium halide, sulfate or phosphate salt thereof as defined in claim 11.

14. A hypotensive composition which comprises a pharmaceutically effective amount of a compound of the formula (Ic) defined in claim 11 or a pharmaceutically acceptable acid addition or quaternary $C_1$–$C_4$-alkyl ammonium halide, sulfate or phosphate salt thereof and a pharmaceutically acceptable carrier.

15. A hyptensive method of treatment which comprises the step of administering to a susceptible animal subject a pharmaceutically effective amount of the compound of the formula (Ic) defined in claim 11 or a pharmaceutically acceptable acid addition or quaternary $C_1$–$C_4$-alkyl ammonium halide, sulfate or phosphate salt thereof.

16. A compound of the formula (Id)

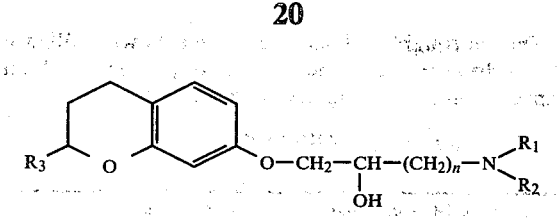

or a pharmaceutically acceptable acid addition or quaternary $C_1$–$C_4$-alkyl ammonium halide, sulfate or phosphate salt thereof where $R_1$ and $R_2$ are each hydrogen, $C_1$ to $C_6$ alkyl, hydroxy-alkyl, alkenyl, cycloalkyl, phenyl-alkyl, or dimethoxy-phenylalkyl;

$R_3$ is $C_1$ to $C_4$ alkyl or phenyl; and n is 1 or 2.

17. The compound of the formula (Id) defined in claim 16 or a pharmaceutically acceptable acid addition or quaternary $C_1$–$C_4$-alkyl ammonium halide, sulfate or phosphate salt thereof selected from the group consisting of (a) 1-(2-methyl-3,4-dihydro-2H-1-benzopyrane-7-yloxy)-3-(1-methyl-ethylamino)-2-propanol;

(b) 1-(2-methyl-3,4-dihydro-2H-1-benzopyrane-7-yloxy)-3-(1,1-dimethyl-ethylamino)-2-propanol;

(c) 1-(2-methyl-3,4-dihydro-2H-1-benzopyrane-7-yloxy)-3-cyclohexylamino-2-propanol;

(d) 4-(1-methyl-ethylamino)-1-(2-methyl-3,4-dihydro-2H-1-benzopyrane-7-yloxy)-2-butanol;

(e) 4-(1,1-dimethyl-ethylamino)-1-(2-methyl-3,4-dihydro-2H-1-benzopyrane-7-yloxy)-2-butanol; and (f) 4-(cyclohexylamino)-1-(2-phenyl-3,4-dihydro-2H-1-benzopyrane-7-yloxy)-2-butanol.

18. 1-(2-methyl-3,4-dihydro-2H-1-benzopyrane-7-yloxy)-3-cyclohexylamino-2-propanol or a pharmaceutically acceptable acid addition or quaternary $C_1$–$C_4$-alkyl ammonium halide, sulfate or phosphate salt thereof as defined in claim 16.

19. A beta-blocking composition which comprises a pharmaceutically effective amount of the compound of the formula (Id) defined in claim 16 or a pharmaceutically acceptable acid addition or quaternary $C_1$–$C_4$-alkyl ammonium halide, sulfate or phosphate salt thereof and a pharmaceutically acceptable carrier.

20. A method of blocking the beta adrenergic receptors in an animal subject which comprises the step of administering to said animal subject a pharmaceutically effective amount of the compound of the formula (Id) defined in claim 16 or a pharmaceutically acceptable acid addition or $C_1$–$C_4$-alkyl quaternary ammonium halide, sulfate or phosphate salt thereof.

21. A compound of the formula (Ie)

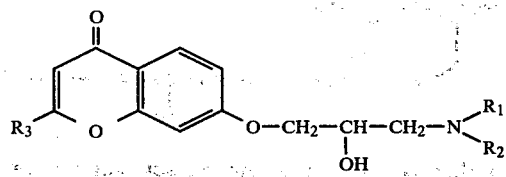

or a pharmaceutically acceptable acid addition or quaternary $C_1$–$C_4$-alkyl ammonium halide, sulfate or phosphate salt thereof, wherein $R_1$ and $R_2$ are each hydrogen, $C_1$ to $C_6$ alkyl, hydroxy-alkyl, alkenyl, cycloalkyl, phenyl-alkyl, or dimethoxy-phenylalkyl; and $R_3$ is hydrogen or $C_1$ to $C_4$ alkyl.

22. A compound of the formula (Ie) as defined in claim 21 selected from the group consisting of
(a) 1-(2-methyl-4H-1-benzopyrane-4-one-7-yloxy)-3-(1-methyl-ethylamino)-2-propanol;
(b) 1-(2-methyl-4H-1-benzopyrane-4-one-7-yloxy)-3-(cyclohexylamino)-2-propanol;
(c) 1-(2-methyl-4H-1-benzopyrane-4-one-7-yloxy)-3-(1,1-dimethyl-ethylamino)-2-propanol;
(d) 1-(2-methyl-4H-1-benzopyrane-4-one-7-yloxy)-3-(2-allylamino)-2-propanol; and
(e) 1-(4H-1-benzopyrane-4-one-7-yloxy)-3-(1,1-dimethyl-ethylamino)-2-propanol; or a pharmaceutically acceptable acid addition or quaternary $C_1$-$C_4$-alkyl ammonium halide, sulfate or phosphate salt thereof.

23. 1-(2-methyl-4H-1-benzopyrane-4-one-7-yloxy)-3-(1,1-dimethyl-ethylamino)-2-propanol or a pharmaceutically acceptable acid addition or quaternary $C_1$-$C_4$-alkyl ammonium halide, sulfate or phosphate salt thereof as defined in claim 21.

24. An antiarrhythmic and hypotensive composition which comprises a pharmaceutically effective amount of the compound of the formula (Ie) defined in claim 21 or a pharmaceutically acceptable acid addition or quaternary $C_1$-$C_4$-alkyl ammonium halide, sulfate or phosphate salt thereof and a pharmaceutically acceptable carrier.

25. An antiarrhythmic and hypotensive method of treatment which comprises the step of administering to an animal subject a pharmaceutically effective amount of the compound of the formula (Ie) defined in claim 21 or a pharmaceutically acceptable acid addition or quaternary $C_1$-$C_4$-alkyl ammonium halide, sulfate or phosphate salt thereof.

26. A compound of the formula

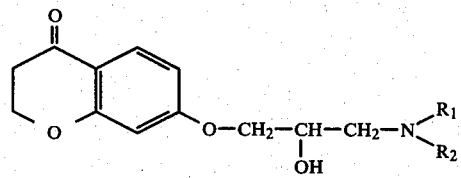

or a pharmaceutically acceptable acid addition or quaternary $C_1$-$C_4$-alkyl ammonium halide, sulfate or phosphate salt thereof, wherein
$R_1$ and $R_2$ are each hydrogen, $C_1$ to $C_6$ alkyl, hydroxyalkyl, alkenyl, cycloalkyl, phenyl-alkyl or dimethoxy-phenyl-alkyl.

27. The compound defined in claim 26 or a pharmaceutically acceptable acid addition or quaternary $C_1$-$C_4$-alkyl ammonium halide, sulfate or phosphate salt thereof, selected from the group consisting of
(a) 1-(2,3-dihydro-4H-1-benzopyrane-4-one-7-yloxy)-3-(1-methyl-ethylamino)-2-propanol;
(b) 1-(2,3-dihydro-4H-1-benzopyrane-4-one-7-yloxy)-3-(1,1-dimethyl-ethylamino)-2-propanol; and
(c) 1-(2,3-dihydro-4H-1-benzopyrane-4-one-7-yloxy)-3-cyclohexyl-amino-2-propanol.

28. 4-cyclohexylamino-1-(2-phenyl-3,4-dihydro-2H-1-benzopyrane-7-yloxy)-2-butanol or a pharmaceutically effective salt thereof.

29. A method of treating a heart disease which comprises administering to a susceptible subject an effective amount of the compound or a pharmaceutically effective salt thereof as defined in claim 28 in dosage form.

* * * * *